(12) United States Patent
Rundle

(10) Patent No.: US 8,664,616 B2
(45) Date of Patent: Mar. 4, 2014

(54) COUNT CORRECTION IN A PHOTON COUNTING IMAGING SYSTEM

(75) Inventor: David S. Rundle, Butler, PA (US)

(73) Assignee: EV Products, Inc., Saxonburg, PA (US)

( * ) Notice: Subject to any disclaimer, the term of this patent is extended or adjusted under 35 U.S.C. 154(b) by 332 days.

(21) Appl. No.: 12/865,218

(22) PCT Filed: Jun. 11, 2009

(86) PCT No.: PCT/US2009/047023
§ 371 (c)(1),
(2), (4) Date: Jan. 14, 2011

(87) PCT Pub. No.: WO2009/155198
PCT Pub. Date: Dec. 23, 2009

(65) Prior Publication Data
US 2011/0101231 A1    May 5, 2011

Related U.S. Application Data

(60) Provisional application No. 61/073,562, filed on Jun. 18, 2008.

(51) Int. Cl.
*G01T 1/20* (2006.01)

(52) U.S. Cl.
USPC ............ 250/370.11; 250/363.09; 250/370.12; 702/85; 702/104; 702/127

(58) Field of Classification Search
USPC ............ 250/363.09, 370.11, 370.12; 702/85, 702/104, 127
See application file for complete search history.

(56) References Cited

U.S. PATENT DOCUMENTS

| 6,753,914 B1* | 6/2004 | Frost ............................. 348/246 |
| 2008/0135771 A1* | 6/2008 | Vydrin et al. ............ 250/370.09 |
| 2008/0267353 A1* | 10/2008 | Rundle ........................... 378/87 |

* cited by examiner

Primary Examiner — Casey Bryant
(74) Attorney, Agent, or Firm — Clark Hill PLC

(57) ABSTRACT

In a method of count correction for pixels of a pixilated photon counting detector, the average count value output by each of a plurality of pixels during a period of time is determined. A product is determined of the actual average count value and a multiplying correction factor. A corrected count value is then determined for the pixel equal to a sum of the product and an additive correction factor. The multiplying correction factor equals a square root of a quotient of a desired average count value to be output by each of the plurality of pixels during the period of time divided by the actual average count value. The additive correction factor equals a product of the multiplying correction factor and the actual average count value subtracted from the desired average count value.

7 Claims, 6 Drawing Sheets

COUNT CORRECTION IN A PHOTON COUNTING IMAGING SYSTEM

BACKGROUND OF THE INVENTION

1. Field of the Invention

The present invention relates to photon detectors and, more particularly, to a system for and method of correcting the pulse count output of each pixel of the photon detector as a function of the incident flux density.

2. Description of Related Art

Current state-of-the-art x-ray imaging systems employ scintillator photodiode arrays to detect and quantify x-rays and gamma rays after they pass through and are attenuated by an object under inspection. Scintillator photodiode arrays include a scintillation material attached to the photodiode array. The scintillation material converts high energy photons (x-rays and gamma rays) into visible or near visible light. This light is then detected by photodiodes in the photodiode array. Scintillation light impinging on each photodiode of the photodiode array is converted thereby into an electrical signal which is amplified and measured to provide an indirect measurement of the incident photon flux.

The operation of a scintillator photodiode array requires a constant influx of photons to deliver a constant scintillation light output (from many photons), thereby producing a photodiode output current that is relatively proportional to the incoming photon flux rate. Scintillator photodiode arrays, therefore, indirectly measure the photon flux by detecting the light emitted by the scintillation material. Consequently, scintillator photodiode arrays do not have the capability to count photons or provide energy information about the detected photons. Notwithstanding, due to their indirect method of measuring photon flux, photodiode arrays can produce a nearly linear response to increasing photon flux.

In contrast to a scintillator photodiode array detector, an energy discriminating photon counting detector can be used to count and discriminate each incoming photon and its energy. A typical photon counting detector includes an array of semiconductor detector elements, e.g., without limitation, CdZnTe, (or pixels) and signal processing electronics. When radiation, such as, without limitation, an x-ray or gamma ray, strikes one of the pixels, charge is generated that is proportional to the energy of the radiation event. The charge generated by the pixel is output thereby as a current or voltage pulse. The radiation event is characterized by the location of the detector element in the array thereof which is struck and the energy of the radiation event. A controller determines this information for every radiation event for all the pixels, accumulates the radiation events occurring during a sample interval of time for all of the pixels into a window or frame, temporarily stores the window or frame in digital form and processes the digital window or frame to form an image.

More specifically, the current or voltage pulse output by each pixel in response to a radiation event (an incoming photon) is compared by a comparator (either directly or after amplification) to a threshold voltage or current. Current or voltage pulses below this threshold value are ignored. In contrast, a count of each current or voltage pulse exceeding this threshold value is accumulated by a controller for processing in a manner known in the art. The counts accumulated from all of the pixels of the photon counting detector for a specific sample interval of time can be converted by the controller in a manner known in the art into an electronic version of an image which can be displayed as a visual image on a display of a imaging system.

As can be seen, a photon counting detector ideally counts each photon individually. Thus, ideally, each voltage or current pulse and the corresponding count accumulated by the controller is in response to a single photon event and the rate that such current or voltage pulses are produced happens at time intervals that permit the comparator utilized to compare the threshold value to the current or voltage pulse to return to baseline between photon events. However, in practice, photons generated by x-ray and gamma ray sources are random in nature. Therefore, as the photon flux increases, the probability of two photons striking the same pixel at or near the same time also increases. In nuclear spectroscopy, this is commonly referred to as a "pulse pileup".

With reference to FIG. 1, a graph 2 showing the output of a single pixel in response to photons striking a pixel of a photon counting detector is shown in relation to a graph 4 of an output of a comparator that is utilized to compare the output of the pixel (either directly or after amplification) to a threshold value 6. As can be seen in corresponding areas 8a and 8b of graphs 2 and 4, respectively, when two or more photons strike the pixel in a short interval of time, the signal output by the comparator does not return to a baseline value before another photon strikes the pixel, whereupon the amplitude of a pulse output by the pixel in response to the other photon striking the pixel is artificially increased by the residual amplitude of the pulse output by the pixel in response to the previous photon striking the pixel. While area 8b of FIG. 1 shows that pulses were counted, one or more of said pulses may not have been greater than or equal to threshold value 6 and, therefore, may not have been counted correctly.

Areas 9a and 9b show that two or more photon pulses received at substantially the same time will result in the output of the amplifier being above threshold 6 for the duration of both photons, whereupon there is no discrimination between each photon striking the corresponding pixel. Similarly, for areas 10a and 10b in FIG. 1.

Both photodiode arrays and photon counting detectors have pixel-to-pixel non-uniformities that produce slightly different sensitivities. The result of non-uniform pixel response to photon flux is lines or streaks in the resulting images. In a photodiode array, the linear response of the detectors allows for a single multiplication factor to be calculated for each pixel to bring all of the pixels in the array to the same mean value for a given constant flux rate. However, this is not the case with a photon counting system as the response is nonlinear and much more difficult to correct.

SUMMARY OF THE INVENTION

Disclosed is a computer-implemented method of count correction for pixels of an energy discriminating pixilated photon counting detector. The method includes (a) storing in the controller a count value desired to be output by each of a plurality of pixels of a pixilated photon counting detector in response to exposure of each pixel thereof to the same photon flux density over a sample period of time; (b) in response to exposure of each pixel of the plurality of pixels to photon flux during the sample period of time, the controller: (b1) determining an actual average count value output by the pixel; (b2) dividing the desired count value in step (a) by the actual average count value of the pixel determined in step (b1) to obtain a quotient therefor; (b3) determining for the pixel a multiplying correction factor equal to a square root of the quotient determined in step (b2); (b4) determining a product of the multiplying correction factor and the actual average count value; (b5) determining for the pixel an additive correction factor equal to the product determined in step (b4)

subtracted from the desired average count value; (b6) summing the additive correction factor to the product of the multiplying correction factor and the actual average count value to obtain a corrected count value for the pixel; and the controller causing the corrected count values to be displayed as a color on a display.

Also disclosed is a controller-implemented method of count correction for pixels of an energy discriminating pixilated photon counting detector comprising, for each of a plurality of pixels of the detector, (a) the controller determining an average count value output by the pixel during a period of time; (b) the controller determining a product of the actual average count value and a multiplying correction factor; (c) the controller determining a corrected count value for the pixel equal to a sum of the product determined in step (b) and an additive correction factor, wherein: the multiplying correction factor equals a square root of a quotient of a desired average count value to be output by the pixel during the period of time divided by the actual average count value; and the additive correction factor is equal to a product of the multiplying correction factor and the actual average count value subtracted from the desired count value; and the controller causing the corrected count value for the pixel to be displayed as a color on a display.

Also disclosed is a computer-implemented method of count correction for pixels of an energy discriminating pixilated photon counting detector comprising, for each of a plurality of pixels of the detector, (a) the controller determining an actual average count value output by the pixel for each of a plurality of different photon flux densities incident on the pixel; (b) the controller determining for each photon flux density a product of the corresponding actual average count value and a multiplying correction factor that is equal to a square root of a quotient of a desired average count value to be output by each of the plurality of pixels at the photon flux density divided by the actual average count value output by the pixel; (c) the controller determining for each photon flux density a corrected count value for the pixel equal to a sum of (1) the product determined in step (b) and (2) an additive correction factor that is equal to the product of the multiplying correction factor determined in step (b) and the actual average count value subtracted from the desired average count value; and the controller causing the corrected count value for the pixel to be displayed as a color on a display.

The method can further include, for an actual average count value output by one of the pixels that is different than any of the actual average count values determined for the pixel in step (a), determining the multiplying and additive correction factors for the pixel via interpolation of the multiplying and additive correction factors determined for the pixel at least at two photon flux density.

Also disclosed is a count correcting radiographic imaging system comprising: a photon source for outputting x-ray photons or gamma ray photons along a transmission path of photons output by said photon source; a photon counting detector array having pixels disposed in the transmission path of the photons output by said photon source; and a controller operative for detecting and processing photon events detected by the pixels of the photon counting detector array, said controller further operative for determining for each pixel an average count value output by the pixel during a period of time; determining a product of the actual average count value and a multiplying correction factor; and determining a corrected count value for the pixel equal to a sum of the product and an additive correction factor, wherein: the multiplying correction factor equals a square root of a quotient of a desired average count value to be output by the pixel during the period of time divided by the actual average count value; and the additive correction factor equals a product of the multiplying correction factor and the actual average count value subtracted from the desired average count value.

The imaging system can include a display operative under the control of the controller for displaying each corrected count value as a color. The color can be either black, white, a shade of gray, or a color other than black, or white, or a shade of gray.

DETAILED DESCRIPTION OF THE INVENTION

The present invention will now be described with reference to the accompanying figures where like reference numbers correspond to like elements.

Figure 2:
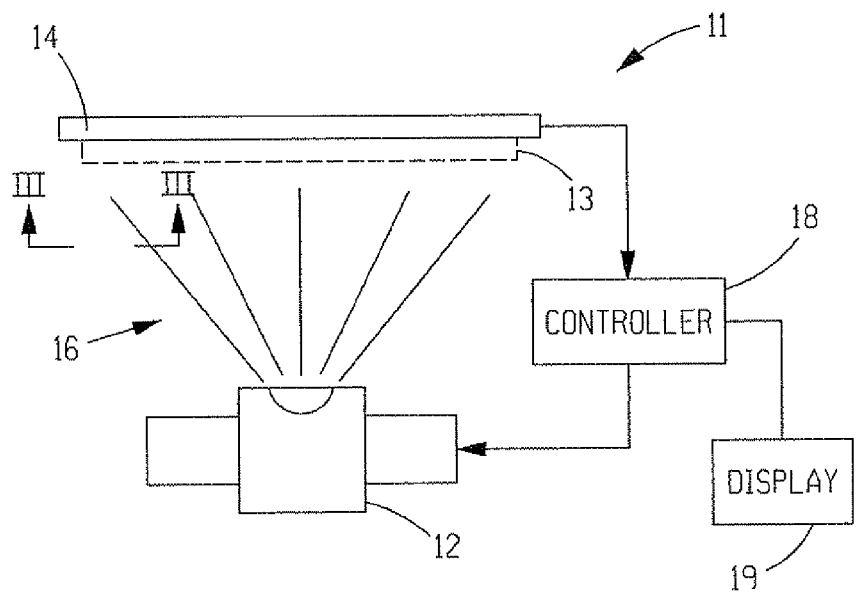
FIG. 2 is a schematic diagram of a radiographic imaging system that includes a high energy photon source and a pixilated photon counting detector positioned in a transmission path of photons output by the photon source.

With reference to FIG. 2, a radiographic imaging system 11 includes a high energy photon source 12, such as, without limitation, an x-ray source or a gamma ray source, and at least one photon counting detector array 14 positioned in a transmission path 16 of photons output by photon source 12. If desired, a collimator (not shown) may be positioned in transmission path 16 between photon source 12 and detector array 14 for shaping, focusing and restricting the photons that impinge on detector array 14.

One or more controllers 18 can be provided and operative for controlling the operation of photon source 12 and for detecting and processing photon events detected by the radiation detection elements or pixels (described hereinafter) of detector array 14 and for performing count correction in the manners described hereinafter. The depiction in FIG. 2 of a single controller 18 coupled to photon source 12 and detector array 14 is not to be construed as limiting the invention since it is envisioned that any number of controllers 18, operating independently or in coordination with each other, can be utilized.

Signal processing electronics, such as one or more comparators for each pixel (not specifically shown) can be provided as standalone components, as an integral part of detector array 14, as an integral part of controller 18, or some combination thereof, as desired. In response to each photon from photon source 12 striking one of the pixels of detector array 14, a charge is generated thereby that is proportional to the energy of the photon. The charge generated in each pixel is output thereby as a current or voltage pulse which is processed by the signal processing electronics. For each pixel, the signal processing electronics determines whether the energy of the photon exceeds one or more threshold values and for all of the pixels accumulates the number of photon events occurring within a sample interval of time into a window or frame that can be processed, along with other windows or frames, by controller 18 into an image of the photons striking detector array 14 during said sample interval. Inasmuch as suitable signal processing electronics are well-known in the art, they will not be described herein for purpose of simplicity.

Figure 3:
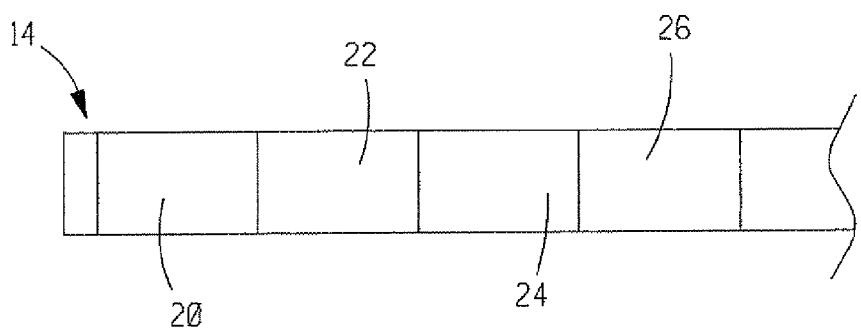
FIG. 3 is an enlarged view of four pixels of the pixilated photon counting detector of FIG. 2 taken along lines III-III in FIG. 2.

With reference to FIG. 3 and with continuing reference to FIG. 2, an enlarged view of four pixels 20-26 of detector array 14 is shown.

Figure 4:
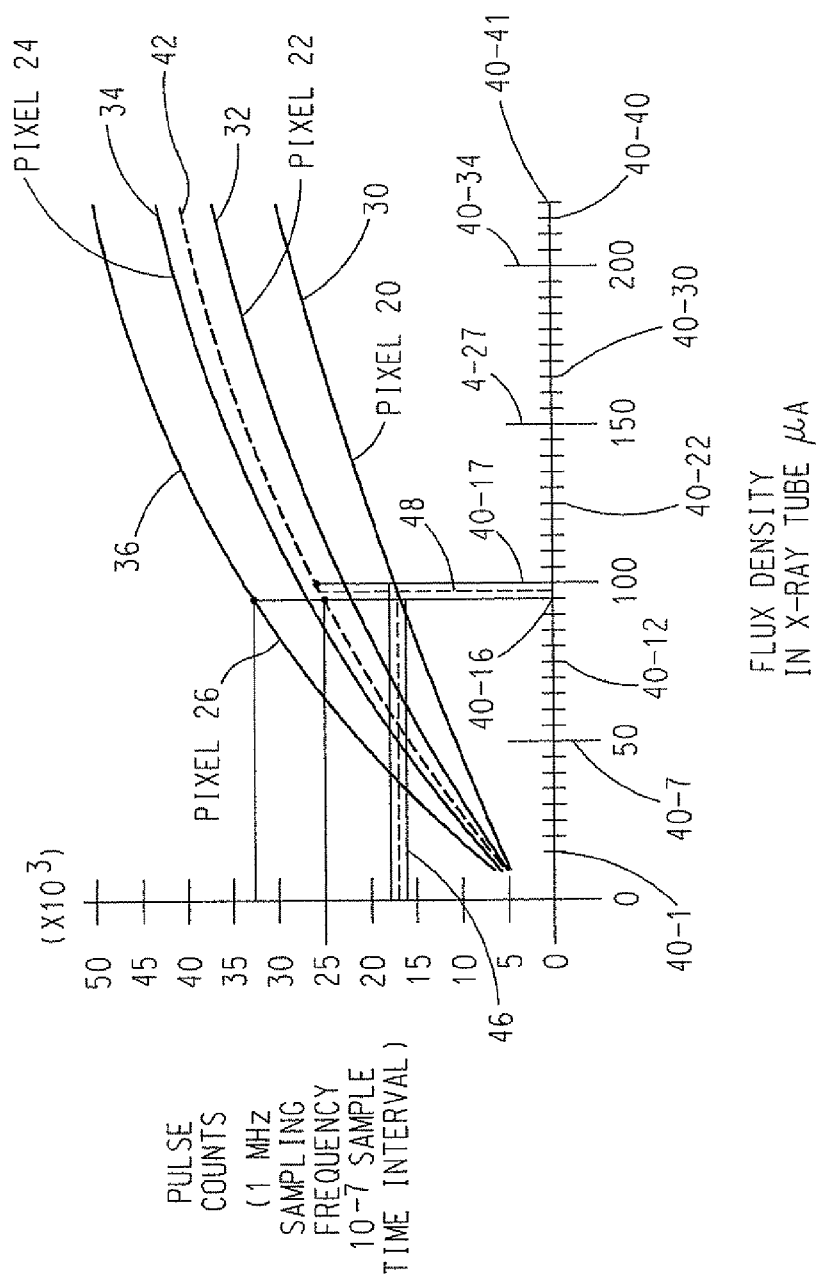
FIG. 4 is a graph of flux density (expressed in x-ray tube current μA) versus pulse counts output by the four pixels shown in FIG. 3.

With reference to FIG. 4 and with continuing reference to FIGS. 2 and 3, plots 30-36 of the response of pixels 20-26, respectively, are shown. Each plot 30-36 shows the number of pulse counts output by the corresponding pixel electronics during a sample interval of time in response to being exposed to an incoming photon flux density expressed in x-ray tube current.

For the purpose of simplicity, the present invention will be described in connection with the response of pixels 20-26. However, this is not to be construed as limiting the invention since the present invention is extensible to a detector array having any number of pixels and/or arrangements thereof.

As can be seen from FIG. 4, each pixel 20-26 can have a unique non-uniform response to the same photon flux density. In order to produce the best possible images, it is necessary that the response of each pixel 20-26, represented by plots 30-36, respectively, be corrected, as necessary, to account for such non-uniformity. To this end, a mean pulse count value of all the pixels 20-26 at each of a plurality of points 40 along the flux density axis in FIG. 4 can be determined. A plot joining all of the thus determined mean pulse count values is shown by dashed line 42 in FIG. 4.

More specifically, the mean value of the photon pulse count for all of the pixels under consideration, e.g., pixels 20-26, is determined for each of points 40-1-40-41 in FIG. 4. Dashed line 42 in FIG. 4 represents a plot of all of the thus determined mean values determined for points 40-1-40-41.

Next, for the response of each pixel 20-26 represented by plots 30-36, respectively, for each point 40-1-40-41, a multiplying correction factor is determined that, when multiplied by a given pulse count value, equals the mean pulse count value determined for all of the pixels at said point 40.

For example, suppose that the flux density at point 40-16 corresponds to a mean value of 25,000 pulses being output by all the pixels during the sample interval. Further, suppose that in practice, pixel 20 (plot 30) outputs 17,000 pulses during the sample interval at a flux density corresponding to point 40-16. Accordingly, the multiplying correction factor for pixel 20 at the flux density corresponding to point 40-16 is 25/17 (25,000/17,000). In contrast, suppose that at the flux density corresponding to point 40-16, pixel 26 (plot 36) outputs 38,000 pulses during the sample interval. The multiplying correction factor for pixel 26 would be 25/38 (25,000/38,000).

The multiplying correction factor determined for each combination of pixel and point 40 is utilized to adjust or correct the actual number of pulses actually output by the pixel to the mean number of pulses for all of the pixels at the flux density corresponding to said point 40. For example, if during a given sample interval, pixel 20 (plot 30) outputs 17,000 pulses, this pulse count will be multiplied by the correction factor 25/17, whereupon the corrected pulse count equals 25,000. Similarly, if pixel 26 (plot 36) outputs 38,000 pulses during the sample interval, this value will be multiplied by the correction factor 25/38 to yield a corrected pulse count of 25,000. Thus, for each combination of pixel and point 40, controller 18 multiplies the actual number of pulses the pixel outputs during a sample interval by the corresponding multiplying correction factor to yield a corrected number of pulse counts equal to the mean number of pulse counts output by all of the pixels at the flux density corresponding to said point 40.

Alternatively, instead of determining each correction factor as a ratio to be multiplied by the number of pulse counts output by the corresponding pixel during a sample interval at a given flux density, the correction factor for each combination of pixel and flux density can be the difference between the actual number of pulse counts output by said pixel and the average number of pulse counts output by all of the pixels over said sample interval at said flux rate, i.e., an additive correction factor.

For example, suppose the average number of pulse counts output by all the pixels at the flux density corresponding to point 40-16 in FIG. 4 is 25,000. Further, suppose pixel 20 (plot 30) outputs 17,000 pulse counts over the same sample interval for the same flux density. The difference between these two values is 8,000 (25,000–17,000) which is stored by controller 18 as the additive correction factor for use in correcting the number of pulse counts output by pixel 20 for the sample time interval at the flux density corresponding point 40-16 in FIG. 4. In a similar manner for pixel 26 (plot 36), the correction factor value of 8,000 (33,000–25,000) can be stored by controller 18 as the additive correction factor for use in correcting the number of pulse counts output by pixel 26 for the sample time interval at the flux density corresponding point 40-16 in FIG. 4.

Utilizing the thus determined additive correction factors for each pixel of detector array 14, controller 18 can correct the number of pulse counts output by each pixel over a given sample time interval and flux density to the average number of pulse counts output by all of the pixels for said time interval and flux density. For example, in response to pixel 26 outputting 33,000 pulse counts during the sample time interval, controller 18 subtracts 8,000 pulse counts, i.e., the additive correction factor –8,000, to arrive at 25,000 pulse counts, i.e., the average number of pulse counts output by all of the pixels for the corresponding flux density. Similarly, in response to pixel 20 outputting 17,000 pulse counts during the sample time interval, controller 18 adds 8,000, i.e., the additive correction factor 8,000, to this value to arrive at 25,000 pulse counts, i.e., the average number of pulse counts output by all of the pixels for the corresponding flux density.

Also or alternatively, combinations of the multiplying and/or additive correction factors described above can be used for different pixels for the same sample interval and flux density.

In the foregoing description, the number of pulse counts output by each pixel during the sample interval was determined at forty-one points 40 (40-1-40-41) for a like number of different flux densities. However, this is not to be construed as limiting the invention since any suitable and/or desirable number of points 40 can be utilized.

In addition, when, in practice, for a given pixel, the number of pulse counts output by said pixel during the sample time interval does not equal the number of pulse counts output by said pixel for a given point 40 corresponding to a given flux density, a suitable mathematical technique, such as interpolation, can be utilized to estimate the corresponding average number of pulse counts and, consequently, the correction factor to be applied. For example, suppose pixel 20 outputs 16,500 pulse counts during the sample time interval. As shown by the dashed line 46 in FIG. 4, 16,500 pulse counts falls between the pulse counts of 16,000 and 17,000 for pixel 20 (plot 30), which correspond to the flux densities associated with points 40-16 and 40-17, respectively. Utilizing any suitable and/or desirable interpolation technique for the correction values of pixel 20 (plot 30) for the flux densities associated with points 40-16 and 40-17, a suitable correction factor can be determined which can be combined (added, subtracted or multiplied) with 16,500 pulse counts to get an estimated average pulse count output by pixel 20 for the flux density shown by dashed line 48 between the flux densities associated with points 40-16 and 40-17.

The foregoing interpolation example is not to be construed as limiting the invention since it is envisioned that any suitable and/or desirable method can be utilized for determining an average number of pulse counts on dashed line 42 between the pulse counts associated with adjacent points 40, e.g., 40-16 and 40-17, to determine the pulse counts therefor. For example, interpolation between the average pulse counts for the average flux densities corresponding to points 40-16 and 40-17 can be utilized to determine the average pulse count for a flux density therebetween.

As discussed above, if desired, the number of points 40 corresponding to the range of flux densities can be increased or decreased. In addition, although points 40 shown in FIG. 4 are spaced uniformly, this is not to be construed as limiting the invention since it is envisioned that the points 40 can be spaced in any suitable and/or desirable manner. For example, in more linear portions of plots 30-36, points 40 can be spaced further apart. In contrast, in more nonlinear portions of plots 30-36, more sample points 40 spaced closer together can be utilized.

Figure 1:
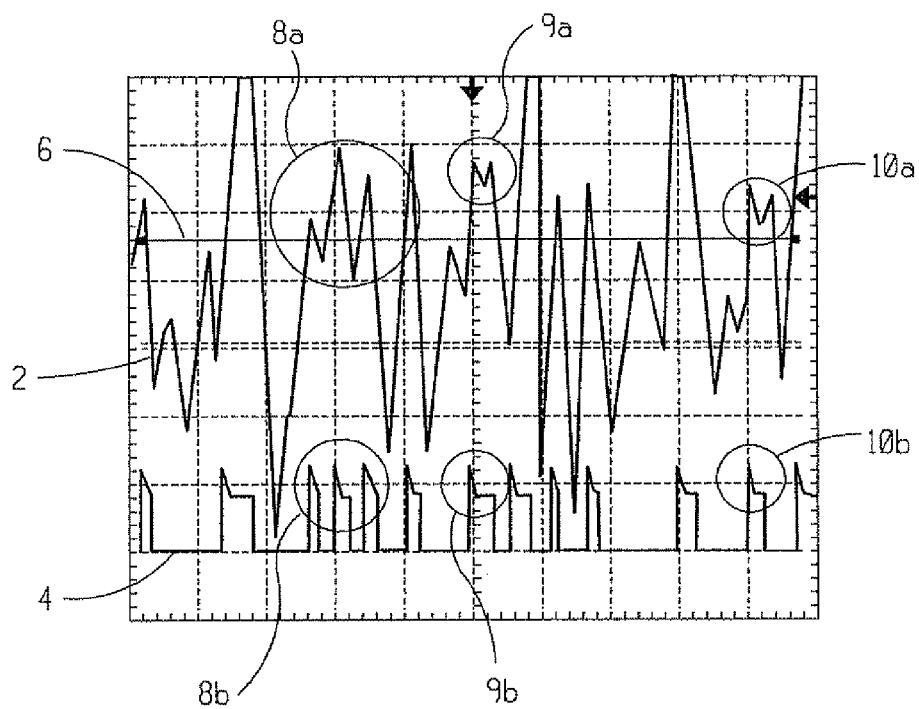
FIG. 1 is a graph (2) showing the output of a single pixel of a pixilated photon counting detector in response to striking photons in relation to a graph (4) of an output of a comparator that is utilized to compare the output of the pixel (either directly or after amplification) to a threshold value (6)

One or more correction factor(s) can be calculated for each combination of pixel and flux density corresponding to a point 40 by changing the electrical energy input into photon source 12 to obtain a desired flux density and then determine the correction factor(s) for this combination of pixel and flux density in one of the manners described above. This method of determining correction factor(s) works well for a single threshold, non-energy discriminating photon counting system. However, when the photon energy for each pulse is separated into a number of discrete energy bins, a desired method of determining correction factors for each bin is to use an attenuator 13 (shown in phantom in FIG. 1) in transmission path 16 between photon source 12 and detector array 14.

Figure 5:
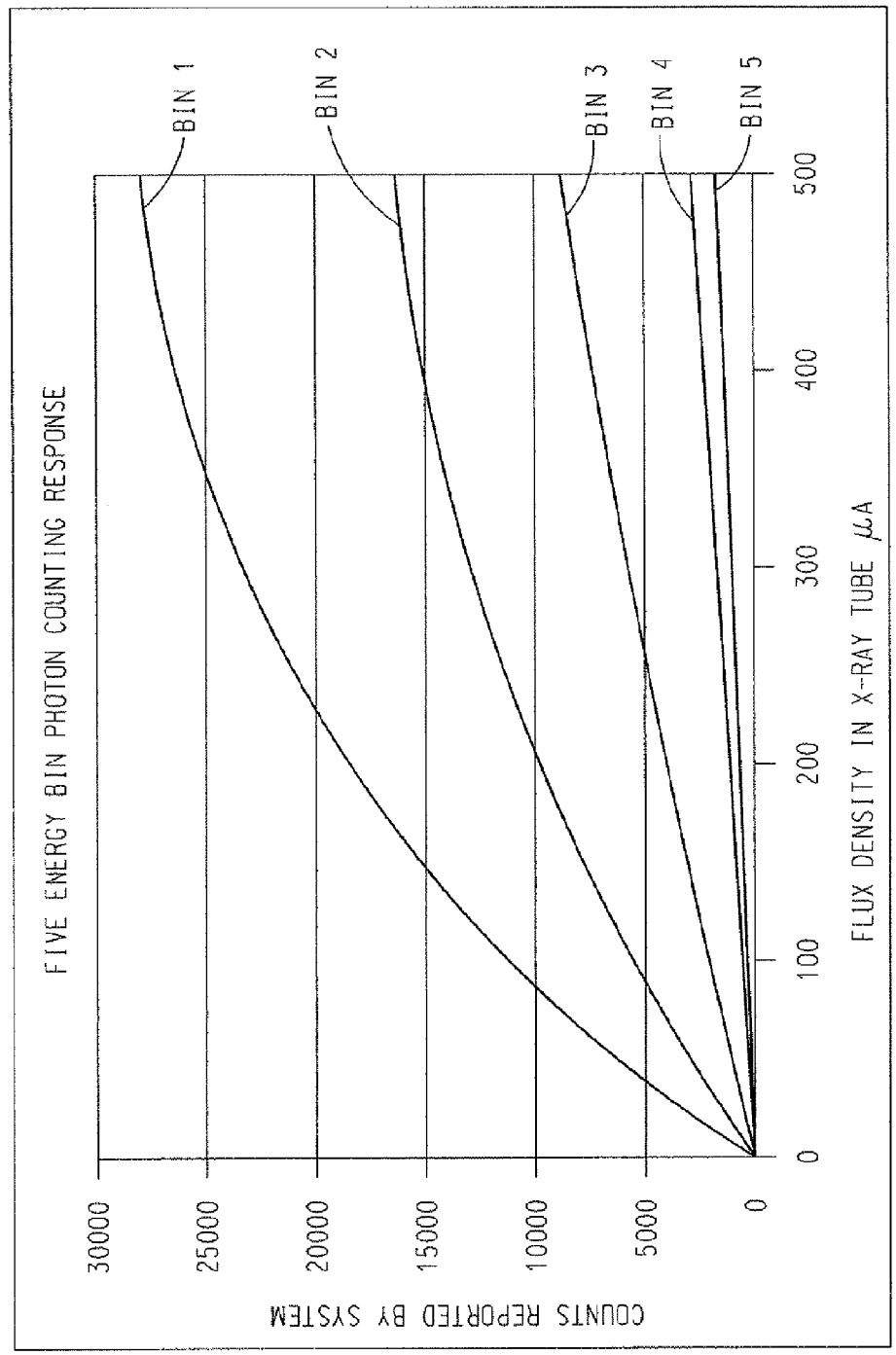
FIG. 5 is a graph of the flux density (expressed in x-ray tube current μA) versus pulse counts shown in FIG. 4 segregated into five discrete energy bins between 25 and 50 keV (Bin 1), 50 and 75 keV (Bin 2), 75 and 100 keV (Bin 3), 100 and 125 keV (Bin 4) and photon energies above 125 keV (Bin 5)

For example, suppose that the pulse counts shown in FIG. 4 are segregated into discrete energy bins between 25 and 50 keV; 50 and 75 keV; 75 and 100 keV; 100 and 125 keV; and photon energies above 125 keV, as shown in FIG. 5. Consequently, each pixel of an imaging array can have five energy bins, each of which will have a unique non-uniform response to a given photon flux density. Therefore, the calculation of five independent correction factors for each of the five energy bins for each individual pixel at each desired correction point is required. In FIG. 5, photon energy values 25 keV, 50 keV, 75 keV, 100 keV and 125 keV are associated with energy bin 5 through bin 1, respectively. However, this is not to be construed as limiting the invention.

When the input power to photon source 12 is varied, the resulting energy spectrum changes uniformly across the entire energy range. This produces correction points that are equally spaced during open beam conditions. However, when system 11 is used for imaging, the reduction in the photon flux for a given amount of power applied to photon source 12 is due to attenuation, which is highly energy dependent and significantly changes the resulting spectrum seen by detector array 14. This can produce points 40 that are not optimally spaced, especially within each energy bin, and, therefore, produce poor results. Accordingly, it is desirable to utilize multiple attenuators 13 to simulate the attenuation in normal operation of system 11 to optimize the placement of points 40. To this end, the material choice and thickness of each attenuator 13 must be chosen with the intended application in mind. The number of points 40 required is also a function of the expected dynamic range of the intended application. Once all of this is taken into consideration, suitable materials and thicknesses of each attenuator 13 can be identified for each desired correction point 40.

In practice, an attenuator 13 having the greatest attenuation can be placed in transmission path 16 as shown in FIG. 2 for determining the correction factors for one of the points, e.g., 40-1, for all of the pixels 20-26; an attenuator 13 having the next greatest attenuation can be placed in transmission path 16 as shown in FIG. 2 for determining the correction factors for the next point, e.g., 40-2, for all of the pixels 20-26; and so forth until no attenuator 13 is in the transmission path 16 for determining the correction factors for the last point, e.g., 40-41, for all of the pixels 20-26.

The correction factors determined for each energy bin can include additive correction factors, multiplying correction factors and/or some combination thereof.

The use of one or more attenuators 13 in transmission path 16 enables correction factors to be determined for each point 40 of each energy bin for a given input of electrical power to photon source 12 that simulates the attenuation expected in normal operation of imaging system 11.

First and Second Moment Correction

Figure 6:
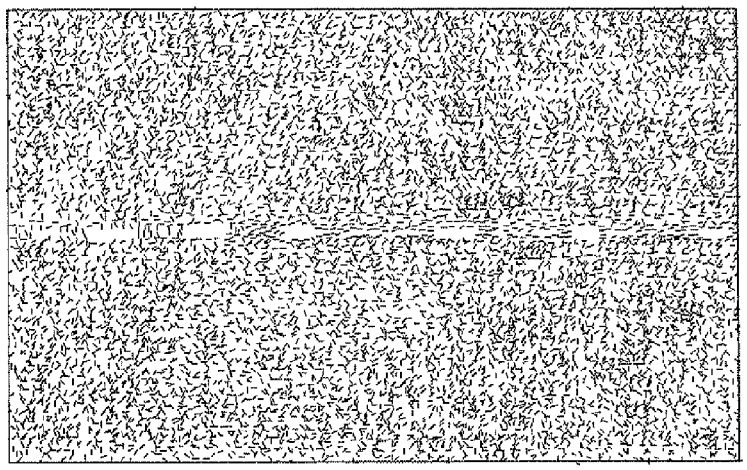
FIG. 6 is an actual image produced via a pixilated photon counting detector utilizing suitable multiplying correction factors that produce the illustrated black and white speckled image including an image artifact (the horizontal line)

With reference to FIG. 6, it has been observed that the use of multiplying correction factors occasionally results in an artifact in an image. In FIG. 6, an image produced by photons striking a two-dimensional array after application of suitable multiplying correction factors desirably produces a black and white, shade of gray, or colored speckled image, also known as a "salt-and-pepper pattern". However, it has been observed that the application of multiplying correction factors occasionally produces an image artifact in the salt-and-pepper pattern, like the horizontal line shown in FIG. 6.

In connection with the use of multiplying correction factors, image artifacts, like the horizontal line shown in FIG. 6, have been determined to result from the inherent distortion in the statistical variance of a count value that has been corrected by multiplication. To this end, the photon flux reaching each pixel of a detector array follows a Poisson distribution. In probability theory and statistics, a Poisson distribution is a discreet probability distribution that expresses the probability of a number of events occurring in a fixed period of time if these events occur with a known average rate and independently of the time since the last event (such as the arrival of photons at a pixel of a detector array).

Knowing that the arrival of photons at a pixel of a detector array follows a Poisson distribution, it can be understood that while a multiplying correction factor accurately corrects differences in count values between individual pixels, such multiplying correction factor distorts the statistical variance (or standard deviation) by the square of the correction factor, i.e., $X^2$. This effect can be better understood with reference to FIGS. 7 and 8.

Figure 7:
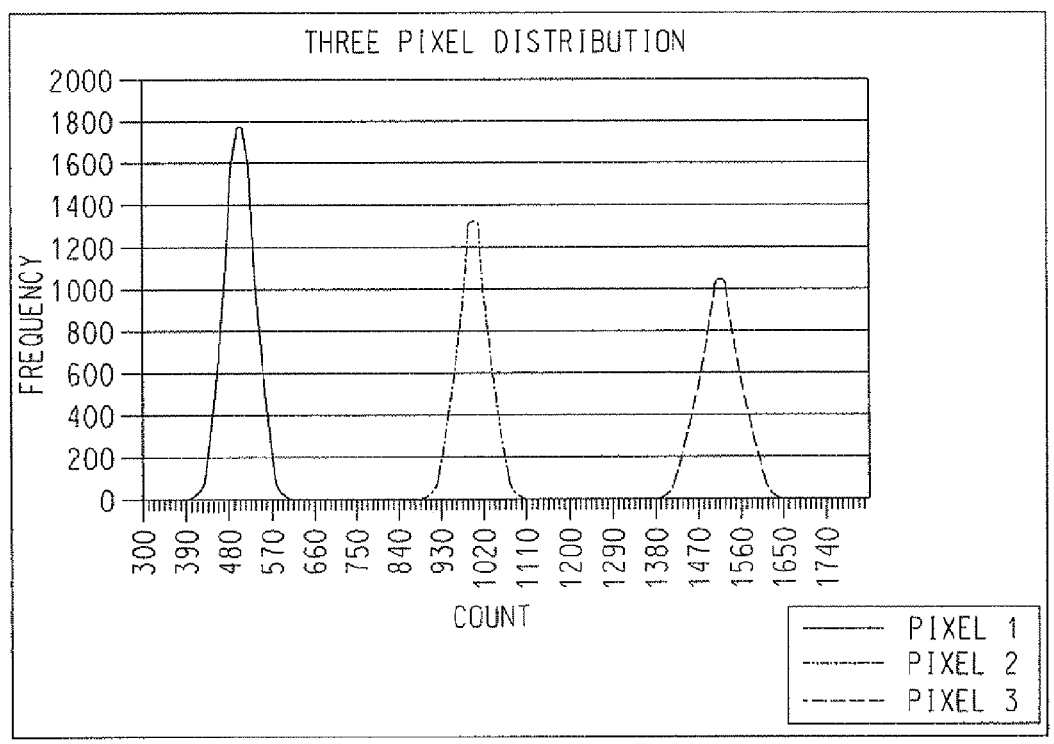
FIG. 7 are plots of frequency (of the occurrence of particular count values) versus count for three pixels of a pixilated detector array for the same sample interval and photon flux density, wherein each plot has a Poisson distribution.

FIG. 7 is a graph of frequency (of the occurrence of particular count values) versus count for three pixels of a pixilated detector array for the same sample interval and photon flux density. In FIG. 7, pixels 1-3 are illustrated as having average count values of 500, 1,000 and 1,500, respectively, for illustration purposes only. Accordingly, these average count values are not to be construed as limiting the invention. As can be seen, for the average count values thereof, pixel 1 produces a larger number of counts than pixel 2 which produces a larger number of counts than pixel 3. In a Poisson distribution, the average count value for each pixel 1-3 is also the standard deviation or variance for the pixel. Hence, pixel 1 has an average count value of 500 and a variance of 500; pixel 2 has an average count value of 1,000 and a variance of 1,000; and pixel 3 has an average count value of 1,500 and a variance of 1,500.

Figure 8:
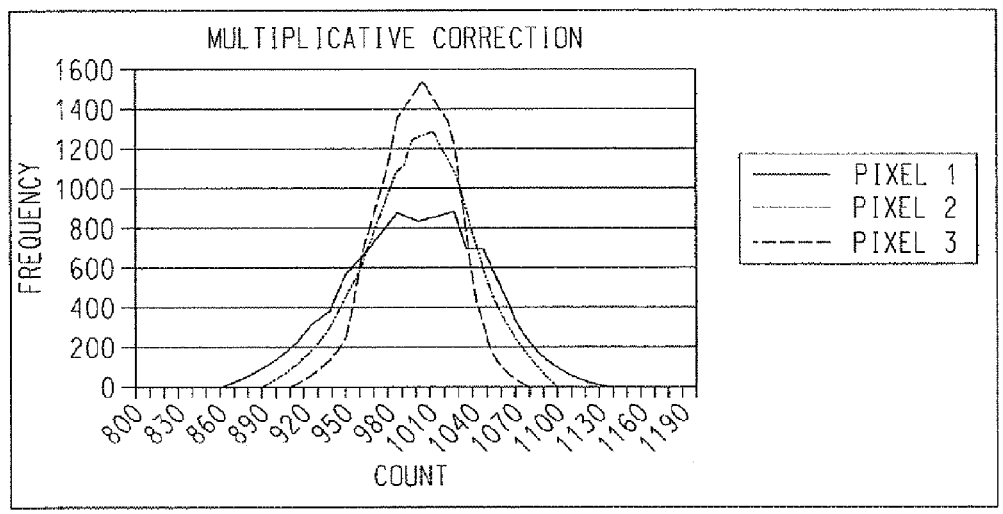
FIG. 8 are plots of frequency (of the occurrence of particular count values) versus count for the three pixels of FIG. 7 after multiplying correction factors are applied to the average count values of the plots of FIG. 7, wherein the plots of FIG. 8 are no longer Poisson or uniform.

To correct pixels 1, 2 and 3 to a uniform 1,000 count average, multiplying correction factors of 2, 1 and 0.667, respectively, would be applied to the count value for each pixel for a given sample interval and flux density. When these multiplicative correction factors are applied to the data sets used to produce the Poisson distributions for pixel 1, 2 and 3 shown in FIG. 7, the distributions shown in FIG. 8 are produced which are no longer Poisson or uniform. To this end, as can be seen in FIG. 8, while the average count value of each pixel is now 1,000, the distributions are no longer uniform. It is believed that this non-uniform distribution results in artifacts in images produced by a multi-pixel detector array.

To overcome this problem, a different correction factor needs to be applied to each pixel count value output by each of a plurality of pixels for the same sample interval and flux density, in the manner discussed above, for the purpose of correcting the variance to the final average count value (a second moment or variance correction). Then, the individual count value can be corrected by the use of an additive correction factor to bring the count value to that of the entire array (a first moment or count sensitivity correction). An example of this two-step correction for pixels 1, 2 and 3 shown in FIGS. 7 and 8 will now be described for these pixels with reference to FIG. 9.

Suppose that pixels 1, 2 and 3 have average count values of 500, 1000 and 1,500. Assuming that it is desired that the average count value and variance of each pixel be 1,000 after correction, the desired variance of the corrected average count value is divided by the variance of the pixel prior to application of the multiplying correction factor and then the square root is taken of that value. For pixel 1, this would be $\sqrt{1000/500}$ or 1.414214; for pixel 2, it would be $\sqrt{1000/1000}$ or 1; and for pixel 3, it would be $\sqrt{1000/1500}$ or 0.816497. These values are the multiplying correction factors for pixels 1, 2 and 3 that are multiplied to the actual average count values to determine the desired average count values for the pixels.

To calculate the additive correction factors for pixels 1, 2 and 3, the actual average count value for each pixel is multiplied by the multiplying correction factor for said pixel determined in the previous paragraph. This product is then subtracted from the desired average count value. For example, for pixel 1 the additive correction factor would be 1,000−(500×1.414214)=292.89; for pixel 2 the additive correction factor is 0; and for pixel 3 the additive correction factor would be 1,000−(1,500×0.816497)=224.745.

Once the multiplying and additive correction factors have been determined for each pixel, the multiplying correction factors can be multiplied with the count values of their respective pixels to correct the variances of the pixels to the final average count value (second moment or variance correction). Then, the additive correction factors for each pixel can be added to the product of the multiplying correction factor and the actual pixel count value to determine a corrected average count value for the pixel (first moment or count sensitivity correction).

For example, applying the multiplying and additive correction factors for pixel 1 to the original count value of 500 for pixel 1 before correction yields a corrected average count value of 500(1.414214)+292.89=999.997. Applying the multiplying and additive correction factors for pixel 2 to the average count value of 1,000 for pixel 2 before correction yields a corrected average count value of 1,000(1)+0=1,000. Lastly, applying the multiplying and additive correction factors for pixel 3 to the average count value of 1,500 for pixel 3 before correction yields a corrected average count value of 1,500(0.816497)−224.745=1,000.0005.

Recalling that in a Poisson distribution, the variance is equal to the mean value, after application of appropriate multiplying and additive correction factors, the corrected average count values for pixels 1, 2 and 3 will also be the variances for pixels 1, 2 and 3. Thus, in this example, pixel 1 will have a corrected average count value and a variance of 999.997; pixel 2 will have a corrected average count value and a variance of 1,000; and pixel 3 will have a corrected average count value and a variance of 1,000.0005.

Figure 9:
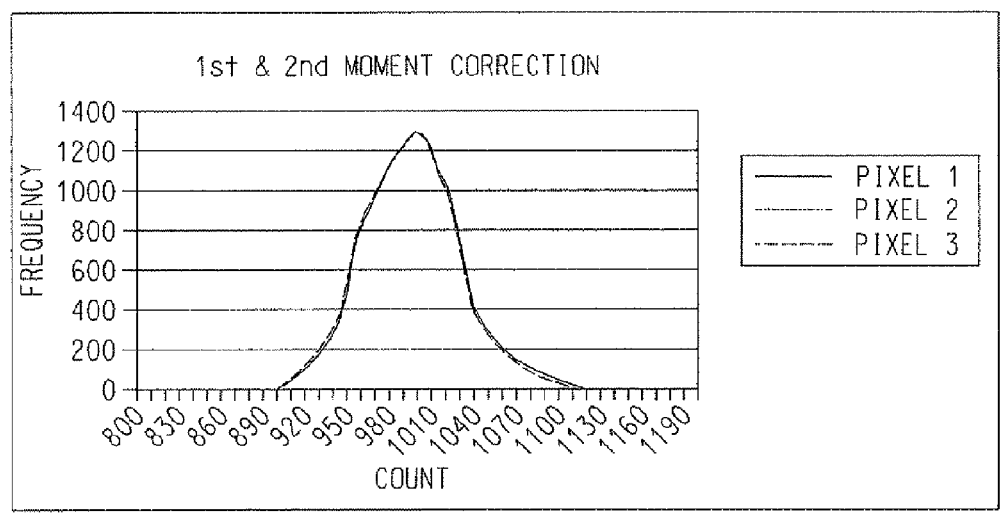
FIG. 9 are plots showing the results of a two-step correction disclosed herein applied to the average count values of three pixels shown in FIG. 7 to produce corrected count values that have Poisson distributions.

Utilizing the foregoing multiplying and additive correction factors for each of pixels 1, 2 and 3 described above, on the data sets utilized to produce the Poisson distributions shown in FIG. 7 for pixels 1, 2 and 3 yields the first and second moment corrected Poisson distributions for pixels 1, 2 and 3 shown in FIG. 9.

With reference back to FIG. 4, the use of multiplying and additive correction factors described above in connection with FIGS. 6-9 will now be discussed with reference to the plots 30-36 of FIG. 4 for the pixels 20-26 of the detector array 14 shown in FIG. 3, respectively.

As discussed above, each pixel 20-26 can have a unique non-uniform response to the same photon flux density. In order to produce the best possible images, it is desirable to determine multiplying and additive correction factors, in the manner described above in connection with FIGS. 6-9, for the response of each pixel at a plurality of points 40 along the flux density axis in FIG. 4. For example, multiplying and additive correction factors (for first and second moment correction) are determined in the manner described above in connection with FIGS. 6-9 for each point 40-1-40-41 in FIG. 4 for each pixel 20-26 represented by plots 30-36, respectively, for a given sample time interval, e.g., $10^{-7}$ seconds.

Thereafter, if the actual number of pulses output by a pixel during a sample time interval corresponds to the number of pulses output by said pixel for which corresponding multiplying and additive correction factors have been determined for a point 40 in the manner described above in connection with FIGS. 6-9, said multiplying and additive correction factors can be applied to the actual count of the pulses output during the sample time interval in the manner described above to determine a corrected average count value that has the same or similar average count value and Poisson distribution as the corrected average pulse count values of the other pixels of the array for the same sample interval and flux density.

Multiplicative and additive correction factors can also be determined in the manner discussed above in connection with FIGS. 6-9 for different pulse counts output by each pixel for different flux densities corresponding to different discrete energy bins, like the discrete energy bins shown in FIG. 5. For example, each pixel can have a unique pair of multiplicative and additive correction factors associated with each discrete energy bin at each desired correction point 40.

In addition, when, in practice, for a given pixel, the actual average pulse counts output by said pixel during the sample time interval does not equal the number of pulse counts output by said pixel for a given point 40 corresponding to a given flux density, a suitable mathematical technique, such as, without limitation, interpolation, can be utilized to determine the corresponding multiplying and additive correction factors to be applied to the actual pulse counts output by the pixel to determine a corrected average pulse count value that has the same Poisson distribution for the same flux density as the other pixels for the same flux density. For example, suppose pixel 20 outputs 16,500 pulse counts during the sample time interval. As shown by dashed line 46 in FIG. 4, 16,500 pulse counts fall between the pulse counts of 16,000 and 17,000 for pixel 20 (plot 30), which corresponds to the flux densities associated with points 40-16 and 40-17, respectively, for which corresponding multiplying (M) and additive (A) correction factors ($M_{16},A_{16}$) and ($M_{17},A_{17}$), respectively, have been determined that will produce corrected pulse count values that have the same corrected average pulse count value and Poisson distribution as the corrected average pulse count values and Poisson distribution determined for all the other pixels of detector array 14 for the same flux density. Utilizing any suitable and/or desirable interpolation technique for the multiplying (M) and additive (A) correction values of pixel 20 for the flux densities associated with points 40-16 and 40-17, suitable multiplying and additive correction factors can be determined which can be combined with the 16,500 pulse counts to determine a corrected average pulse count value for pixel 20 that has the same corrected average pulse count value and Poisson distribution as corrected pulse count values and Poisson distributions determined for pixels 22, 24 and 26 determined in the same manner for the same flux density and sample time interval. For example, without limitation, the multiplying and additive correction factors for pixel 20 (plot 30 in FIG. 4) for 16,500 pulse counts can be the average of the multiplying and additive correction factors for points 40-16 and 40-17, for 16,000 pulse counts and 17,000 pulse counts, respectively, (i.e., $M_{16.5}=(M_{16}+M_{17})/2$ and $A_{16.5}=(A_{16}+A_{17})/2$). The use of any other suitable and/or desirable interpolation technique is also envisioned.

In FIG. 4, the number of points 40 corresponding to the range of flux densities for which multiplying and additive correction factors that produce a proper corrected average pulse count values and Poisson distributions can be increased or decreased as desired. In addition, although points 40 shown in FIG. 4 are spaced somewhat uniformly, this is not to be construed as limiting the invention since it is envisioned that points 40 can be spaced in a suitable and/or desirable manner. For example, in more linear portions of plots 30-36, points 40 can be spaced further apart. In contrast, in more non-linear portions of plots 30-36, more points 40 spaced closer together can be utilized.

Multiplying and additive correction factors that produce corrected average pulse count values that have corrected Poisson distributions can be calculated for each combination of pixel and flux density corresponding to points 40-1-40-41. This can be accomplished by changing the electrical energy input into photon source 12 to obtain desired flux densities at detector array 14 and then determining the corresponding multiplying and additive correction factors for each pixel at each point 40-1-40-41 that produce desired corrected average pulse count value and Poisson distribution for this combination of pixel and flux density in the manner described above. This method of determining multiplying and additive correction factors works well for a single threshold, non-energy discriminating photon counting system. However, when the photon energy for each pulse is separated into one of a number of discreet energy bids, a desired method of determining multiplying and additive correction factors for each combination of point 40 and pixel 20-26 is to use attenuator 13 (shown in phantom in FIG. 1) in transmission path 16 between photon source 12 and detector array 14.

When the input power to photon source 12 is varied, the resulting energy spectrum changes uniformly across the entire energy range. This produces correction points that are equally spaced during open beam conditions. However, when system 11 is used for imaging, the reduction in photon flux for a given amount of power applied to source 12 is due to attenuation, which is highly energy dependent and significantly changes the resulting spectrum seen by detector 14. This can produce points 40 that are not optimally spaced and, therefore, produce poor results. Accordingly, it is desirable to use multiple attenuators 13 to simulate the attenuation seen by detector array 14 during normal operation of system 11 to optimize the placement of points 40. To this end, the material choice and thickness of each attenuator 13 must be chosen with the intended application in mind. The number of points 40 required is also a function of the expected dynamic range of the intended application. Once all of this is taken into consideration, suitable materials and thicknesses of each attenuator 13 can be identified for each desired correction point 40. In practice, an attenuator 13 having the greatest attenuation can be placed in transmission path 16 as shown in FIG. 2 for determining the multiplying and additive correction factors for one of the points, e.g., 40-1, for all of the pixels 20-26; the attenuator 13 having the next greatest attenuation can be placed in transmission path 16 as shown in FIG. 2 for determining the multiplying and additive correction factors for the next point, e.g., 40-2; for all of the pixels 20-26, and so forth until no attenuator 13 is in transmission path 16 for determining the multiplying and additive correction factors for the last point, e.g., 40-41, for all of the pixels 20-26.

The use of one or more attenuators in transmission path 16 enables multiplying and additive correction factors to be determined for each point 40 for a given input of electrical power to photon source 12 that simulates the attenuation expected in normal operation of imaging system 10.

Controller 18 can be operative for performing the various steps of count correction utilizing additive correction factors, multiplying correction factors or the combination (or pair) of additive and multiplying correction factors in any of the manners discussed above. For example, controller 18 can include a controller, such as a microprocessor, operating under the control of a software program that causes controller 18 to correct the pulse counts counted for each pixel during each sample interval utilizing one of the appropriate correction factors described above, and for displaying on display 19 an image corresponding to the corrected count values. Controller 18 can be operative for utilizing a single additive or multiplying correction factor or the combination (or pair) of multiplying and additive correction factor(s) described above for the entire energy range that can be detected by each pixel. Alternatively, controller 18 can be operative for utilizing a different single additive or multiplying correction factor or a single pair of the combination of additive and multiplying correction factors for each of a number of discrete energy ranges that can be detected by each pixel at each point. Thus, for example, if at each point 40, controller is operative for classifying detected radiation events into five discrete energy bins, controller 18 can have one multiplying or additive correction factor or one pair of multiplying and additive correction factors that is/are utilized for each such energy bin.

As can be seen, a system for and method of correcting for non-uniform pixel response in a photon counting detector is provided, whereupon the appearance of lines or streaks in images produced by radiation events detected by said detector can be avoided.

The present invention has been described with reference to the preferred embodiments. Obvious modifications and alterations will occur to others upon reading and understanding the preceding detailed description.

The invention claimed is:

1. A controller-implemented method of count correction for pixels of an energy discriminating pixilated photon counting detector, the method comprising:
   (a) storing in the controller a count value desired to be output by each of a plurality of pixels of a pixilated photon counting detector in response to exposure of each pixel thereof to the same photon flux density over a sample period of time;
   (b) in response to exposure of each pixel of the plurality of pixels to photon flux during the sample period of time, the controller:
      (b1) determining an actual average count value output by, the pixel;
      (b2) dividing the desired count value in step (a) by the actual average count value of the pixel determined in step (b1) to obtain a quotient therefore;
      (b3) determining for the pixel a multiplying correction factor equal to a square root of the quotient determined in step (b2);
      (b4) determining a product of the multiplying correction factor and the actual average count value;
      (b5) determining for the pixel an additive correction factor equal to the product determined in step (b4) subtracted from the desired average count value; and
      (b6) summing the additive correction factor to the product of the multiplying correction factor and the actual average count value to obtain a corrected count value for the pixel; and
   (c) the controller causing the corrected count values to be displayed as a color on a display.

2. A controller-implemented method of count correction for pixels of an energy discriminating pixilated photon counting detector comprising, for each of a plurality of pixels of the detector:
   (a) the controller determining an average count value output by the pixel during a period of time;
   (b) the controller determining a product of the actual average count value and a multiplying correction factor;
   (c) the controller determining a corrected count value for the pixel equal to a sum of the product determined in step (b) and an additive correction factor; and
   (d) the controller causing the corrected count value for the pixel to be displayed as a color on a display, wherein:
      the multiplying correction factor equals a square root of a quotient of a desired average count value to be output by the pixel during the period of time divided by the actual average count value; and
      the additive correction factor is equal to a product of the multiplying correction factor and the actual average count value subtracted from the desired average count value.

3. A controller-implemented method of count correction for pixels of an energy discriminating pixilated photon counting detector comprising, for each of a plurality of pixels of the detector:
   (a) the controller determining an actual average count value output by the pixel for each of a plurality of different photon flux densities incident on the pixel;
   (b) the controller determining for each photon flux density a product of the corresponding actual average count value and a multiplying correction factor that is equal to a square root of a quotient of a desired average count value to be output by each of the plurality of pixels at the photon flux density divided by the actual average count value output by the pixel;
   (c) the controller determining for each photon flux density a corrected count value for the pixel equal to a sum of (1) the product determined in step (b) and (2) an additive correction factor that is equal to the product of the multiplying correction factor determined in step (b) and the actual average count value subtracted from the desired average count value; and
   (d) the controller causing the corrected count value for the pixel to be displayed as a color on a display.

4. The method of claim 3, further including, for an actual average count value output by one of the pixels that is different than any of the actual average count values determined for the pixel in step (a), determining the multiplying and additive correction factors for the pixel via interpolation of the multiplying and additive correction factors determined for the pixel at least at one photon flux density.

5. A count correcting radiographic imaging system comprising:
   a photon source for outputting x-ray photons or gamma ray photons along a transmission path of photons output by said photon source;
   a photon counting detector array having pixels disposed in the transmission path of the photons output by said photon source; and
   a controller operative for detecting and processing photon events detected by the pixels of the photon counting detector array, said controller being programmed with instructions, the instructions when executed by the controller, performing the steps of:
      determining for each pixel an average count value output by the pixel during a period of time;
      determining a product of the actual average count value and a multiplying correction factor, wherein the multiplying correction factor equal a square root of a quotient of a desired average count value to be output by the pixel during the period of time divided by the actual average count value; and
      determining a corrected count value for the pixel equal to a sum of the product and an additive correction factor, wherein the additive correction factor equals a product of the multiplying correction factor and the actual average count value subtracted from the desired average count value.

6. The imaging system of claim 5, further including a display operative under the control of the controller for displaying each corrected count value as a color.

7. The imaging system of claim 6, wherein the color is either black, white, a shade of gray, or a color other than black, or white, or a shade of gray.

* * * * *